US011008617B2

(12) United States Patent
Golestaneh

(10) Patent No.: US 11,008,617 B2
(45) Date of Patent: May 18, 2021

(54) BIOMARKERS AND THERAPEUTIC TARGETS FOR ABNORMAL RETINAL PIGMENT EPITHELIUM

(71) Applicant: GEORGETOWN UNIVERSITY, Washington, DC (US)

(72) Inventor: Nady Golestaneh, Bethesda, MD (US)

(73) Assignee: GEORGETOWN UNIVERSITY, Washington, DC (US)

( * ) Notice: Subject to any disclaimer, the term of this patent is extended or adjusted under 35 U.S.C. 154(b) by 62 days.

(21) Appl. No.: 15/113,444

(22) PCT Filed: Jan. 23, 2015

(86) PCT No.: PCT/US2015/012644
§ 371 (c)(1),
(2) Date: Jul. 22, 2016

(87) PCT Pub. No.: WO2015/112837
PCT Pub. Date: Jul. 30, 2015

(65) Prior Publication Data
US 2017/0022562 A1   Jan. 26, 2017

Related U.S. Application Data

(60) Provisional application No. 61/931,192, filed on Jan. 24, 2014, provisional application No. 61/948,150, filed on Mar. 5, 2014.

(51) Int. Cl.
*C12Q 1/6883* (2018.01)
*C12N 15/113* (2010.01)
*C12Q 1/6851* (2018.01)

(52) U.S. Cl.
CPC .......... *C12Q 1/6883* (2013.01); *C12N 15/113* (2013.01); *C12N 2310/113* (2013.01); *C12N 2310/141* (2013.01); *C12Q 2600/106* (2013.01); *C12Q 2600/178* (2013.01)

(58) Field of Classification Search
None
See application file for complete search history.

(56) References Cited

U.S. PATENT DOCUMENTS

| 8,455,454 B2 | 6/2013 | Wang et al. |
| 8,568,971 B2 | 10/2013 | Brown et al. |
| 2010/0292310 A1 | 11/2010 | Kelley et al. |
| 2013/0065951 A1 | 3/2013 | Shen et al. |
| 2013/0236425 A1 | 9/2013 | Laughlin et al. |

FOREIGN PATENT DOCUMENTS

WO   2012/078558 A2   6/2012

OTHER PUBLICATIONS

Wang et al (FASEB J. 24, 1552-1571 (2010)) (Year:2010).*
Foulds (Eye (1992) 6, 11-27) (Year: 1992).*
Campochiaro (J Mol Med (2013) 91:311-321) (Year: 2013).*
Sayadi et al (Case Rep Ophthalmol 2017;8:245-249) (Year: 2017).*
Klettner et al (Journal of Biochemistry & Cell Biology 45 (2013) 1457-1467) (Year: 2013).*
Kovacs et al., "MicroRNAs in early diabetic retinopathy in streptozotocin-induced diabetic rats," Investigative Ophthalmology & Visual Science, 52(7):4402-4409 (2011).
Alge-Priglinger et al., "Inhibition of human retinal pigment epithelial cell attachment, spreading, and migration by the human lectin galectin-1," Molecular Vision, 15: 2162-2173 (2009).
Aktas et al., "Relationship between CD107a expression and cytotoxic activity," Cellular Immunology, 254:149-154 (2009).
International Search Report issued in the corresponding International Application No. PCT/US2015/012644 dated Apr. 15, 2015.

* cited by examiner

*Primary Examiner* — Richard A Schnizer
(74) *Attorney, Agent, or Firm* — Haug Partners LLP

(57) ABSTRACT

The present invention relates to markers and therapeutic targets of abnormal retinal pigment epithelium (RPE).

9 Claims, 4 Drawing Sheets

Specification includes a Sequence Listing.

A

| | | |
|---|---|---|
| HOMO SAPIENS (HUMAN) | UGGACGGAGAACUGAUAAGGGU | SEQ ID NO: 2 |
| CANIS LUPUS FAMILIARIS (DOG) | UGGACGGAGAACUGAUAAGGGC | SEQ ID NO: 3 |
| CULEX QUINQUEFASCIATUS (HOUSE MOSQUITO) | UGGACGGAGAACUGAUAAGGGU | SEQ ID NO: 4 |
| CRICETULUS GRISEUS (CHINESE HAMSTER) | UGGACGGAGAACUGAUAAGGGC | SEQ ID NO: 5 |
| CYPRINUS CARPIO (COMMON CARP) | UGGACGGAGAACUGAUAAGGGU | SEQ ID NO: 6 |
| BOS TAURUS (COMMON CATTLE) | UGGACGGAGAACUGAUAAGGGC | SEQ ID NO: 7 |
| DROSOPHILA MELANOGASTER (FRUITFLY) | UGGACGGAGAACUGAUAAGGGU | SEQ ID NO: 8 |
| EQUUS CABALLUS (HORSE) | UGGACGGAGAACUGAUAAGGGU | SEQ ID NO: 9 |
| GALLUS GALLUS (JUNGLEFOWL) | UGGACGGAGAACUGAUAAGGGU | SEQ ID NO: 10 |
| MUS MUSCULUS (MOUSE) | UGGACGGAGAACUGAUAAGGGU | SEQ ID NO: 11 |
| PONGO PYGMAEUS (ORANGUTAN) | UGGACGGAGAACUGAUAAGGGU | SEQ ID NO: 12 |

SEED SEQUENCE

*FIG. 1A*

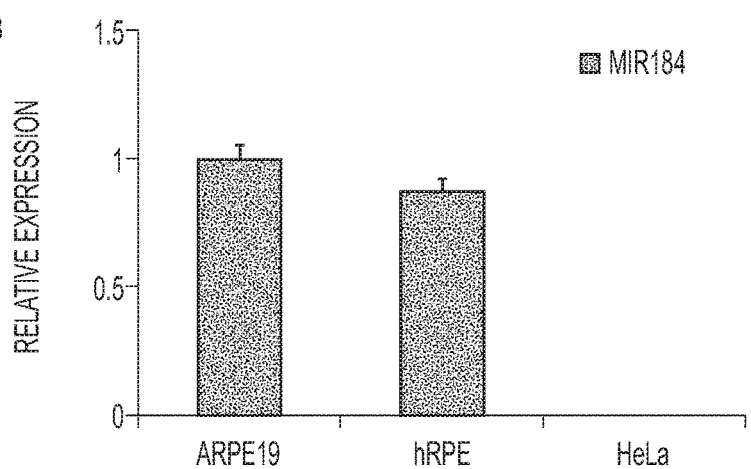

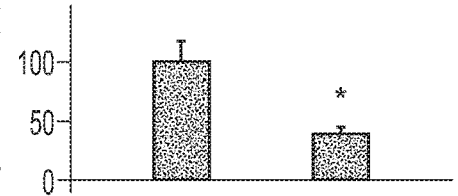

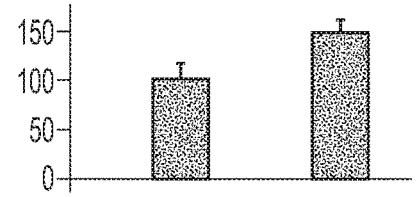

HUMAN EZR mRNA 3'UTR SEQUENCE AND PUTATIVE BINDING SITE FOR hsa-miR-184 SEED SEQUENCE 5'-CAGCCAGGCCAGGACCAAGGGCAGAGGGGTGCTCATAGCGGGCGCTGCCAGCCCCGCCACGCTT
GTGTCTTTAGTGCTCCAAGTCTAGGAACTCCCTCAGATCCCAGTTCCTTTAGAAAGCAGTTACCCAACA
GAAACATTCTGGGCTGGGAACCAGGGAGGCGCCCTGGTTTGTTTTCC CCAGTTGTAATAGTGCCAAG
CAGGCCTGATTCTCGCGATTATTCTCGAATCACCTCCTGTGTTGTGCTGGGAGCAGGACTGATTGAATT
ACGGAAAATGCCTGTAAAGTCTGAGTAAGAA ACTTCATGCTGGCCTGTGTG ATACAAGAGTCAGCATC
ATTAAAGGAAACGTGGCAGGACTTCCATCTGTGCCATACTTGTTCTGTATTCGAAATGAGCTCAAATTGA
TTTTTTAATTTCT ATGAAGGATCCATCTTTGTATATTTACATGCTTAGAGGGGTGAAAATTATTTTTGGAAAT
TGAGTCTGAAGCACTCTCGCACACACAGTGATTCCCTCCTCCCGTCACTCCACGCAGCTGG CAGAGA
GCACAGTGATCACCAGCGTGAGTGGTGGAGGAGGACACTTGGATTTTTTTTTTTGTTTTTTTTTTTTTTG
CTTAACAGTTTTAGAATACATTGTACTTATACACCTTATTAATG ATCAGCTATATACTATTTATATACAAGTG
ATAATACAGATTTGTAACATTAGTTTTAAAAAGGGAAAGTTTTGTTCTGTATATTTGTTACCTTTTACAGAA
TAAAAGAATTACATATGA AAAACCCTCTAAACCATGGCACTTGATGTGATGTGGCAGGAGGGCAGTGGT
GGAGCTGGACCTGCCTGCTGCAGTCACGTGTAAACAGGATTATTATTAGTGTTTTATGCATGTAATGGAC
TATGCACACTTTTAATTTTGTCAGATTCACACATGCCACTATGAGCTTTCAGACTCCAGCTGTGAAGAGA
CTCTGTTTGCTTGTGTTTGTTTGTTTGCAGTCTCTCTCTCTGCCATGGCCT TGGCAGGCTGCTGGAAGCC
AGCTTGTGGAGGCCGTTGGTTCCGCCCACTCATTCCTTCTCGTGCACTGCTTTCTCCTTCACAGCTAAG
ATGCCATGTGCAGGTGGATTCCATGCCGCAGA CATGAAATAAAAGCTTTGCAAAGGCACGAAGCAAAAA
AAAAAAAAAAAAAAAAAAA-3'

SEQ ID NO: 13

FIG. 2C

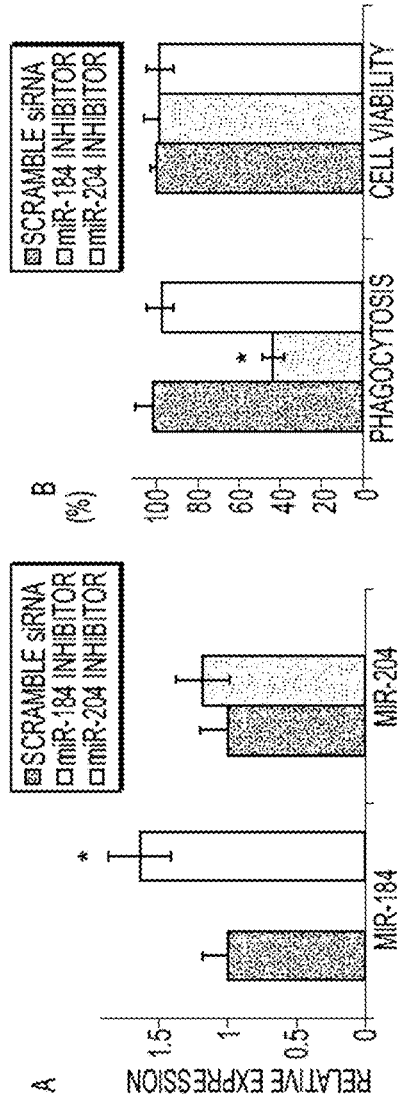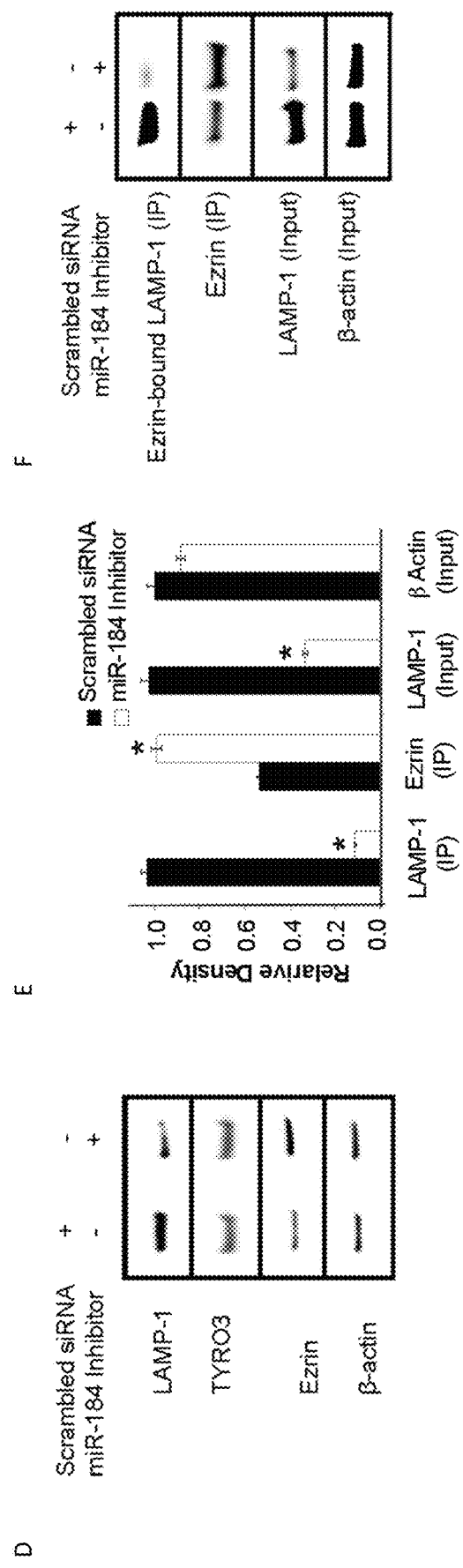

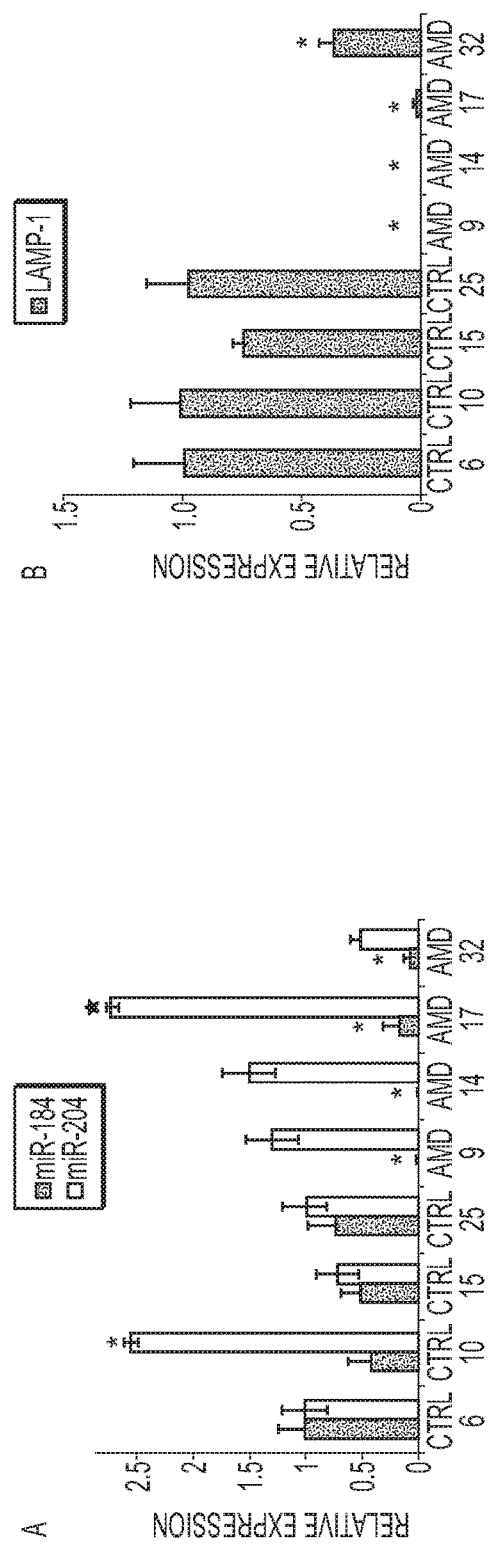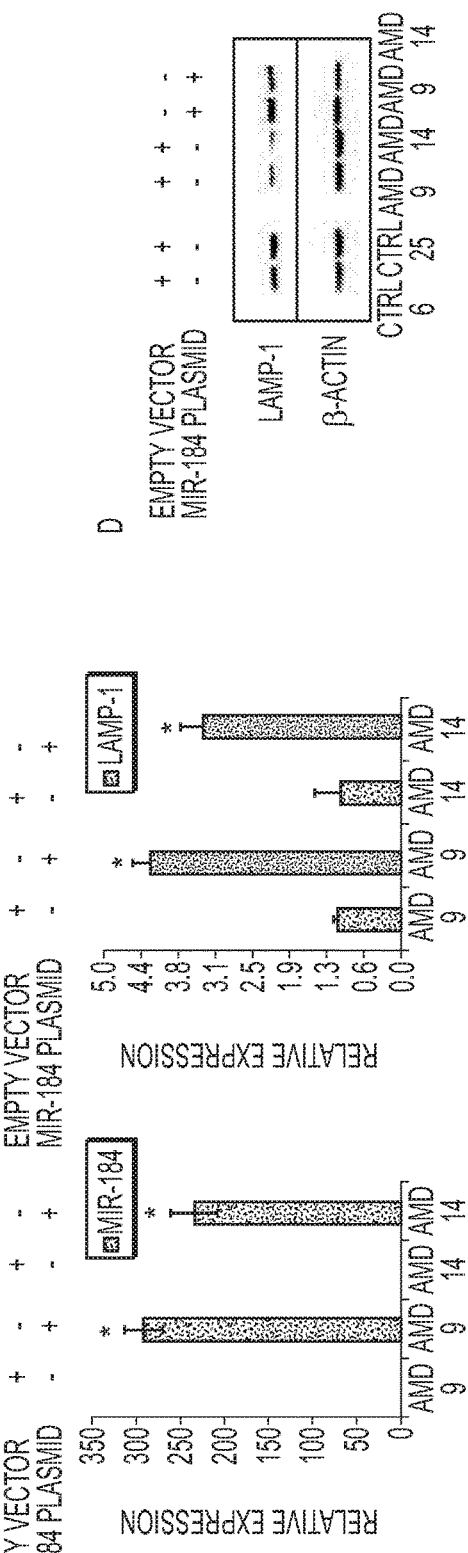
FIG. 4A
FIG. 4B
FIG. 4C
FIG. 4D

BIOMARKERS AND THERAPEUTIC TARGETS FOR ABNORMAL RETINAL PIGMENT EPITHELIUM

SEQUENCE LISTING SUBMISSION VIA EFS-WEB

A computer readable text file, entitled "033681-5030-SequenceListing.txt," created on or about 12 Jun. 2017 with a file size of about 2.4 kb contains the sequence listing for this application and is hereby incorporated by reference in its entirety.

STATEMENT REGARDING FEDERALLY SPONSORED RESEARCH OR DEVELOPMENT

N/A

BACKGROUND OF THE INVENTION

Field of the Invention

The present invention relates to markers and therapeutic targets of abnormal retinal pigment epithelium (RPE).

Background of the Invention

MicroRNA 184 (miR-184) is a highly conserved, short, non-coding RNA molecule that posttranscriptionally regulates protein translation and the function of other micro RNAs (miRNAs). The location of the MIR-184 gene has been mapped to the region 25.1 on the q-arm of chromosome 15 (1). The expression pattern of MIR184 gene and maturation of the final miR-184 is highly regulated and is tissue- and developmental stage-specific (2,3). The repression of the MIR-184 gene is partly carried out by DNA methylation factors such as Methyl-CpG binding protein 1 (MBD1) (4). While primary transcripts and precursors of miR-184 have been detected in many tissue types (1,2,5-7), mature miR-184 is only highly enriched in mouse brain (8), suprabasal cells of the mouse corneal epithelium (9), and zebrafish lens, where it is known to target mediators of neurological development, apoptosis, and cell differentiation (9,10). Furthermore, miR-184 has been implicated in germline development of Drosophila melanogaster (11).

Age-related macular degeneration (AMD) is the leading cause of vision loss among people over age of 50 in developed countries affecting approximately 30-50 million people worldwide (56, 57, 58) and its prevalence is expected to double by 2050 (59).

AMD initially affects the Retinal pigment epithelium (RPE), a monolayer of pigmented and polarized central nervous system (CNS) tissue, and over time leads to secondary loss of photoreceptor cells (60, 61, 56).

AMD is a multifactorial disease (59) and its pathogenesis remains elusive. Mounting evidence suggests a complex interaction of genetic, environmental, and metabolic factors contributing to the pathology of AMD (62). Impairment of RPE function in dry AMD can induce formation of abnormal extracellular deposits called drusen that accumulate between the RPE and Bruch's membrane (BM), and is a hallmark of the disease (63). The wet form of AMD involves choroidal neovascularization accompanied by subsequent formation of a disciform scar (64).

The retinal pigment epithelium (RPE) is a monolayer of pigmented and polarized cells; the apical site of RPE is in close proximity to the outer segments of photoreceptors that are phagocytosed (12), and the basolateral membrane is opposed to Bruch's membrane and the choroid blood supply (13). The RPE play important roles in retinal homeostasis, including formation of the blood/retina barrier (14,15) light absorption (16,17), isomerization of the retinol in the visual cycle (18,19), transportation of nutrients such as glucose, retinol and fatty acids from blood to the photoreceptors (19,20), transportation of ions and water from subretinal space to the blood (21), establishment of immune privilege of the eye (22), and secretion of growth factors (23,24).

Ezrin is a member of the Ezrin, Radixin, Moesin (ERM) proteins family that are reported to act as linkers between the cytoskeleton and plasma membrane (25). Ezrin plays a role in the regulation of cellular adhesion, movement and morphology in epithelia (26) and functions as a protein-tyrosine kinase substrate in microvilli (25,27). Alterations in the expression of Ezrin and other members of ERM family have also been observed in several types of cancer including breast cancer (28), osteosarcoma (29) and brain tumors (30). EZR protein functions by directly binding to proteins including LAMP-1 (also known as CD107a) (31), CD44 (32) and the actin cytoskeleton (33). The molecular interaction of EZR with CD44 and LAMP-1 is required for the metastatic functions, the formation of phagocytic vacuoles (34), vesicular sorting (31,35). LAMP-1 is a membrane glycoprotein that is a key structural component of the lysosomal membrane along with LAMP-2 (36). Deficiencies in both LAMPs are associated with an increased accumulation of autophagic vacuoles in mouse embryonic fibroblasts (35). Human RPE exhibit a cell-type specific tandem expression of mature miR-184 (37, 2). However, the role of miR-184 in RPE is poorly understood.

SUMMARY OF THE INVENTION

The present invention relates to methods of determining if the retinal pigment epithelium (RPE) of a subject having RPE is abnormal, the methods comprising measuring levels of microRNA-184 (miR-184) in RPE obtained from the subject, and comparing the measured levels of miR-184 in the RPE obtained from the subject with normal levels of miR-184, to determine if the subject's levels of miR-184 in RPE are reduced compared to the normal levels of miR-184. A decrease in the levels of miR-184 compared to normal levels of miR-184 is indicative that the subject's RPE is abnormal. In one embodiment, the subject is at risk of developing AMD.

The present invention also relates to methods of determining if a subject has an increased risk developing an abnormal RPE, with the methods comprising measuring levels of miR-184 in RPE obtained from the subject, and comparing the measured levels of miR-184 in the RPE obtained from the subject with normal levels of miR-184, to determine if the subject's levels of miR-184 in RPE are reduced compared to the normal levels of miR-184. A decrease in the levels of miR-184 compared to normal levels of miR-184 is indicative that the RPE of the subject is at risk of becoming abnormal.

The present invention also relates to methods of monitoring the effectiveness of an ocular therapy in a subject receiving the ocular therapy, the methods comprising measuring levels of miR-184 in RPE obtained from the subject receiving the ocular therapy at various time points, and comparing the measured levels of the miR-184 in the RPE at two or more different time points to determine if the levels of miR-184 in RPE in the subject receiving the ocular therapy are increasing over time. An increase in the levels of the miR-184 in the RPE over time is indicative that the ocular therapy is not ineffective. In one embodiment, the subject has AMD or is at risk of developing AMD.

The present invention also relates to engineered retinal pigment epithelial (RPE) cells comprising an exogenous nucleic acid coding for miR-184.

The present invention also relates to methods of treating abnormal retinal pigment epithelium (RPE) in a subject in need of treatment thereof, the method comprising administering to the subject a therapeutically effective amount of miR-184. In one embodiment, the subject is developing AMD.

BRIEF DESCRIPTION OF THE DRAWINGS

FIG. 1 depicts evolutionary conservation and expression of miR-184 in human retinal pigmented epithelial cells (RPE). A. Alignment of the miR-184 nucleotide sequences of various species from insects to humans revealed that miR-184 is highly conserved especially in the seed sequence (underlined). B. qRT-PCR showing that human MIR-184 is expressed in human native RPE, adult ARPE19 cell line, but not in the HeLa cell line.

FIG. 2 depicts that miR-184 binds to the EZR mRNA 3'UTR and regulates the expression of EZR. A. Luciferase assay performed on HeLa cells transfected with Luciferase-EZR 3'UTR construct with and without ectopically expressed MIR-184, showing significantly reduced luciferase activity in the cotransfected HeLa cells (p-value<0.01, n=6). B. Luciferase assay performed on ARPE19 cells transfected with Luciferase-EZR 3'UTR construct with and without treatment with miR-184 inhibitor (hairpin) showing significantly increased luciferase activity in the co-transfected ARPE19 cells (p-value<0.01, n=6). C. Human EZR mRNA 3'UTR containing a putative binding site (underlined) for the miR-184 seed sequence.

FIG. 3 depicts that miR-184 controls phagocytosis in human RPE by modulating the expression of EZR, LAMP-1. A. Transfection of ARPE19 with the miR-184 inhibitor but not with the control (scrambled) siRNA resulted in complete silencing of MIR-184 gene, as shown by qRT-PCR analysis 72 hrs after transfection. B. Phagocytosis assay performed in human native RPE transfected either with scrambled siRNA or with the miR-184 inhibitor, showed significantly reduced phagocytosis efficiency in the presence of the miR-184 inhibitor, 72 hrs after transfection, while the cell viability was not affected. The asterisk indicates statistically significant difference in phagocytosis efficiency (p-value<0.01, n=6). C. qRT-PCR analysis on mRNA from ARPE19 cells transfected with scrambled siRNA or with the miR-184 inhibitor showing significantly up-regulated EZR expression and down-regulated LAMP-1 and TYRO-3 expression levels (p-values<0.01, n=3), 72 hrs after transfection, whereas MERTK and AXL levels remained unchanged. D. Western blot analysis on protein samples isolated from human ARPE19 cells transfected with scrambled siRNA or with the miR-184 inhibitor, showing reduced LAMP-1 and increased Ezrin protein expression. TYRO3 levels were not affected. E. Immunoprecipitation analysis of protein samples from ARPE19 transfected with scrambled siRNA or with the miR-184 inhibitor, followed by precipitation with anti-Ezrin. Ezrin-bound LAMP-1 (IP) as well as total LAMP-1 protein (Input) were significantly decreased in the presence of the miR-184 inhibitor. Densitometry analysis of western blot is shown. Asterisks indicate statistically significant differences, as determined by the t-test (p-value<0.05). F. Immunoprecipitation analysis of protein samples from ARPE19 transfected with scrambled siRNA or with the miR-184 inhibitor, followed by precipitation with anti-Ezrin. Western blot is shown. Beta actin levels in D, E, and F are shown for normalization.

FIG. 4 depicts that MIR-184 and LAMP-1 are down-regulated in the RPE of donors with AMD compared to the RPE of normal donors. A. qRT-PCR analysis of the MIR-184 and MIR-204 levels in RNA samples from four normal (control) primary RPE cultures and four AMD RPE cultures, showing significant down-regulation of MIR-184 in the AMD RPE while the MIR-204 levels do not exhibit such a down regulation. B. qRT-PCR analysis of the LAMP-1 in the same RNA samples as in A, showing significant down-regulation of LAMP-1 in the AMD RPE. C. Expression of MIR-184 and LAMP-1 was restored in the AMD 9 and AMD 14 RPE, following transfection with the MIR-184 overexpressing plasmid, but not with the empty vector, as shown by qRT-PCR analysis. The reactions in A, B and C were performed in triplicates. Asterisks in A and B indicate significantly lower MIR-184 (A) and LAMP-1 (B) mRNA levels in the AMD samples compared to control samples, as determined by the t-test (p-values<0.05, n=3). Asterisks in C indicate statistically significant increase in expression levels of MIR-184 and LAMP-1 after transfection of AMD 9 and AMD 14 RPE with the MIR-184 overexpressing plasmid (p-values<0.05, n=3). D. Western blot analysis of the AMD 9 and AMD 14 RPE transfected with either the MIR-184 overexpressing plasmid or with an empty vector, showing restoration of normal LAMP-1 protein levels only in the presence of the MIR-184 overexpressing plasmid. Normal RPE cultures (Ctrl 6 and Ctrl 25), transfected with an empty vector are shown for comparison. Beta actin equal levels are shown for normalization.

DETAILED DESCRIPTION OF THE INVENTION

The present invention relates to methods of determining if the retinal pigment epithelium (RPE) of a subject having RPE is abnormal, with the methods comprising measuring levels of microRNA-184 (miR-184) in RPE obtained from the subject, and comparing the measured levels of miR-184 in the RPE obtained from the subject with normal levels of miR-184, to determine if the subject's levels of miR-184 in RPE are reduced when compared to the normal levels of miR-184. A decrease in the levels of miR-184 compared to normal levels of miR-184 is indicative that the subject's RPE is abnormal. In one embodiment, the subject is at risk of developing AMD.

As used herein, retinal pigment epithelium, or retinal pigment epithelial cells (either referred to herein as RPE) is a pigmented epithelial cell layer located between the blood vessels of the choriocapillaris and the photoreceptive cells. Phenotypic and functional characteristics of normal, healthy RPE cells include but are not limited to, presence or expression of melanin, presence or expression of pigment epithelium-derived factor (PEDF), presence of expression of RPE65, presence or expression of cellular retinaldehyde binding protein (CRALBP), presence or expression of bestrophin, presence or expression of Pax6 (although Pax6 is normally downregulated mature RPE cells), in the Na+/K+-ATPase being localized apically in the plasma membrane, the extracellular matrix metalloproteinase inducer (EMMPRIN) being located apically, N-CAM being located apically, αvβ5 integrin being located apically, chloride-bicarbonate exchange transporter being located basolaterally, Ca+-sensitive chloride channels being located basolaterally, syntaxin 2 (isoforms 2A and 2B) being located basolaterally, reduction or absence of syntaxin 3 expression, presence or expression of orthodentical homeobox 2 (OTX2), presence or expression of LIM homeobox 2 (LHX2), presence or expression of ectonucleoside triphosphate diphosphohydrolase 2 (ENTPD2), polarized secretion of vascular endothelial growth factor (VEGF), ability to form and maintain tight junctions, presence of a transepithelial potential (TEP), ability to perform phagocytosis, ability to form a confluent monolayer in culture, to name a few. Other characteristics of RPE cells include, but are not limited to those characteristics discussed in Kokkinaki, M., et al., *Stem Cells*, 29:825-835 (2011), which is incorporated by reference.

The invention is not limited to the quality or quantity of characteristics of RPE cells. The term "functional RPE cells," means the cells at least have the ability to efficiently perform phagocytosis, ability to perform autophagy, express melanin and express RPE65. Of course, functional RPE cells can possess additional characteristics consistent with native RPE cells, such as those discussed in Kokkinaki, M., et al., *Stem Cells*, 29:825-835 (2011). In one embodiment of the present invention, the term "abnormal RPE" means that the cells have at least lost the ability to efficiently perform phagocytosis. The ability to perform phagocytosis or autophagy need not be completely absent for the RPE to be considered abnormal. Of course, the ability to perform phagocytosis and autophagy may also be completely absent for the RPE cells to be considered abnormal. In general, one of skill in the art will be able to determine if RPE cells have lost the ability to efficiently perform phagocytosis and autophagy, such that the test RPE would be judged as abnormal. The novelty and inventiveness of the present invention are not dependent on the way in which one of skill will assess if RPE cells are abnormal.

The ability of the RPE cells to efficiently perform phagocytosis can be determined in a cell culture environment using standard, commercially available of phagocytosis assays. The ability of the RPE cells to efficiently perform autophagy can be determined in a cell culture environment using standard, techniques. The ability to assess or diagnose dysfunctional phagocytosis in vivo can be assessed by measuring or observing the presence of drusen, which is a well-known hallmark of AMD and highly suggestive of abnormal phagocytosis or autophagy, In general, one of skill in the art can assess the ability of the test RPE cells to efficiently perform phagosytosis using routine methods, and these results are compared to the ability of RPE cells considered to have a "normal" ability to efficiently perform phagoyctosis, i.e., "control" RPE cells. Any differences in the ability of the test RPE cells to efficiently perform phagocytosis with this same ability in the control RPE cells may be used to conclude that the test RPE cells have a diminished ability to efficiently perform phagocytosis and are thus considered abnormal for the purposes of the present invention.

In another embodiment of the present invention, the term "abnormal RPE" means that the RPE cells have decreased expression levels of express RPE65 as compared to levels observed in normal RPE cells. Expression levels of express RPE65 in RPE cells can be determined in a cell culture environment using standard, commercially available of assays. Examples of ways of measuring expression levels of RPE65 include measuring protein levels, measuring the levels of the mRNA transcript, measuring levels of staring material, product or by-product for which the biochemical pathway of RPE65 protein is involved, e.g., measuring levels of all-trans retinol (starting compound) and 11-cis retinol (end compound). For example, failure of all-trans retinol to be converted to 11-cis retinol at normal rates, as shown by a remainder of all-trans retinol or by lack of production of 11-cis retinol in the assay, would indicate that the RPE cells are abnormal. The RPE cells need not have both a decrease in the ability to efficiently perform phagocytosis and a decrease in RPE65 expression levels to be considered "abnormal." Of course, the RPE cells would be considered abnormal if the cells have both a decrease in the ability to efficiently perform phagocytosis and a decrease in RPE65 expression levels.

In yet another embodiment of the present invention, the term "abnormal RPE" means that the RPE cells have decreased expression levels of express LAMP-1 as compared to levels observed in normal RPE cells. Expression levels of express LAMP-1 in RPE cells can be determined in a cell culture environment using standard, commercially available of assays. Examples of ways of measuring expression levels of LAMP-1 include measuring protein levels and measuring the levels of the mRNA transcript.

As used herein, the term subject or "test subject" indicates an animal, such as but not limited to a mammal. Examples of subjects include human or non-human primates, dogs, cats, horses, sheep, cattle, and the like. Specifically, a subject can be any animal that has pigmented cells in its light-detecting organs. To date, every known eye in the animal kingdom has pigmented epithelial cells. The subjects on which the methods and treatments of the present invention may be performed may or may not have been diagnosed as having or having a predisposition to a condition marked by an abnormal RPE.

In one embodiment, for example, prior to performing the methods of the present invention, the subject has been diagnosed as having a condition or having been exposed to injuries or conditions that are associated with an abnormal retina, abnormal retinal function or an ocular disease, such as but not limited to age-related macular degeneration (AMD), retinitis pigmentosa (RP) or lysosomal storage disease. In another embodiment, prior to performing the methods of the present invention, the subject may have been diagnosed as having an increased risk of developing a condition that is associated with an abnormal retina, abnormal retinal function or an ocular disease, such as but not limited to age-related macular degeneration (AMD) or retinitis pigmentosa (RP). For example, the subject may be diagnosed as a diabetic.

In another embodiment, prior to performing the methods of the present invention, the subject has not been identified as a subject as having a condition or having been exposed to injuries or conditions that are associated with an abnormal retina, abnormal retinal function or an ocular disease, such as but not limited to age-related macular degeneration (AMD) or retinitis pigmentosa (RP). In yet another embodiment, prior to performing the methods of the present invention, the subject has not been diagnosed as having an increased risk of developing a condition that is associated with an abnormal retina, abnormal retinal function or an ocular disease, such as but not limited to age-related macular degeneration (AMD) or retinitis pigmentosa (RP). The AMD can be either "wet" or "dry" AMD, and the general term "AMD" is not limited herein to one specific type of AMD.

As used herein, "abnormal retina" or "abnormal retinal function" may be used interchangeably and can be used to mean conditions in which the retina, or a portion thereof, such as but not limited to, the macula, the fovea and the optic disk, is physically abnormal or is functioning abnormally.

Examples of ocular conditions marked by an abnormal retina or abnormal retinal function include but are not limited to AMD, RP, cone-rod dystrophy, hypertensive retinopathy, diabetic retinopathy, retinoblastoma, retinal dysplasia, retinal atrophy and retinal degeneration to name a few.

With respect to the methods of treatment described herein, the subject being treated is in need of treatment of a condition associated with an abnormal RPE, such as but not limited to AMD or RP. Thus, prior to administering the pharmaceutically effective amounts of the therapeutic compounds described herein, i.e., miR-184, to the subject, the subject is diagnosed with a condition associated with an abnormal RPE, such as but not limited to AMD (wet or dry) or RP.

In some embodiments of the present invention, levels of microRNA-184 (miR-184) are measured. The mature miR-184 transcript in humans is normally 84 bases in length, and it is currently believed that miR-184 does not code for a protein or polypeptide. As used herein, miR-184 is used to mean an RNA transcript comprising or, in the alternative, consisting of the polynucleotide sequence of SEQ ID NO:1. Of course, the polynucleotide sequence of the cDNA version (reverse transcript) of the RNA of SEQ ID NO:1 is identical to the polynucleotide sequence of SEQ ID NO:1, except that the uracil ("u") bases are replaced with thymine ("t") bases. Accordingly, the phrase "polynucleotide sequence" when used in connection with miR-184 (SEQ ID NO:1) can mean the RNA sequence or the cDNA sequence.

ccagucacgu ccccuuauca cuuuuccagc ccagcuuugu gacuguaagu guuggacgga gaacugauaa ggguagguga uuga (SEQ ID NO:1)

In certain embodiments, the miR-184 used in the diagnostic and monitoring methods of the present invention is an RNA molecule or cDNA molecule comprising a polynucleotide sequence that is at least about 83%, 84%, 85%, 86%, 87%, 88%, 89%, 90%, 91%, 92%, 93%, 94%, 95%, 96%, 97%, 98%, 99% or 100% identical to the polynucleotide sequence of SEQ ID NO:1. In one embodiment, the miR-184 used in the diagnostic and monitoring methods of the present invention is an RNA molecule or a cDNA molecule consisting of the polynucleotide sequence of SEQ ID NO:1.

A nucleic acid having a polynucleotide sequence at least, for example, about 95% "identical" to a reference polynucleotide sequence, e.g., SEQ ID NO:1, is understood to mean that the polynucleotide sequence of the nucleic acid molecule is identical to the reference polynucleotide sequence except that the polynucleotide sequence may include up to about five modifications per each 100 nucleotides of the reference polynucleotide sequence. In other words, to obtain a nucleic acid having a polynucleotide sequence at least about 95% identical to a reference polynucleotide sequence, up to about 5% of the nucleotides of the reference sequence may be deleted or substituted with nucleotide or a number of nucleotides up to about 5% of the total nucleotides in the reference sequence may be inserted into the reference sequence. These modifications of the reference sequence may occur at the 5'-terminus or 3'-terminus positions of the reference polynucleotide sequence or anywhere between those terminal positions, interspersed either individually among nucleotides in the reference sequence or in one or more contiguous groups within the reference sequence.

As used herein, "identity" is a measure of the identity of polynucleotide sequences compared to a reference polynucleotide sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there are several methods to measure identity between two polynucleotide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), ExPASy, BLASTN, FASTA (Atschul, S. F., et al., J Molec Biol 215:403 (1990)) and FASTDB.

In one embodiment of the present invention, the algorithm used to determine identity between two or more nucleic acids is BLASTN. The result of sequence alignment is in percent identity. If the reference sequence is shorter or longer than the query sequence because of 5'-terminus or 3'-terminus additions or deletions, but not because of internal additions or deletions, a manual correction can be made, because the BLASTN program does not account for 5'-terminus or 3'-terminus truncations or additions of the reference sequence when calculating percent identity. For query sequences truncated at the 5'-terminus or 3'-terminus, relative to the reference sequence, the percent identity is corrected by calculating the number of bases of the query sequence that are 5'-terminus or 3'-terminus to the reference sequence that are not matched/aligned, as a percent of the total bases of the query sequence. The results of the BLASTN sequence alignment determine matching/alignment. The alignment percentage is then subtracted from the percent identity, calculated by the BLASTN program to arrive at a final percent identity score. This corrected score can be used for the purposes of determining how alignments "correspond" to each other, as well as percentage identity. Bases of the reference sequence that extend past the 5'-terminus or 3'-terminus of the query sequence may be considered for the purposes of manually adjusting the percent identity score. That is, bases that are not matched/aligned with the 5'-terminus or 3'-terminus of the comparison sequence may be counted when manually adjusting the percent identity score or alignment numbering.

For example, a 90-base nucleic acid query sequence is aligned with a 100-base reference sequence to determine percent identity. The deletion occurs at the 5'-terminus of the query sequence and therefore, the BLASTN alignment does not show a match/alignment of the first 10 bases at the 5'-terminus. The 10 unpaired bases represent 10% of the reference sequence (number of bases at the 5'-terminus or 3'-terminus not matched/total number of bases in the reference sequence) so 10% is subtracted from the percent identity score calculated by the BLASTN program. If the remaining 90 bases were perfectly matched (100% alignment) the final percent identity would be 90% (100% alignment 10% unmatched overhang). In another example, a 90 base query sequence is compared with a 100 base sequence, except that the deletions are internal deletions. In this case the percent identity calculated by BLASTN is not manually corrected, since there are no bases at the 5'-terminus or 3'-terminus of the subject sequence that are not matched/aligned with the query. In still another example, a 110-base nucleic acid query sequence is aligned with a 100-base reference sequence to determine percent identity. The addition in the query occurs at the 5'-terminus of the query sequence and therefore, the BLASTN alignment may not show a match/alignment of the first 10 bases at the 5'-terminus. If the remaining 100 bases of the query sequence have 95% identity to the entire length of the reference sequence, the 5'-terminus addition of the query would be ignored and the percent identity of the query to the reference sequence would be 95%.

The diagnostic and monitoring methods of the present invention described herein require assessing or measuring levels of miR-184 in RPE cells. The assessment of the levels of miR-184 can be expressed as absolute or relative values and may or may not be expressed in relation to another component, a standard an internal standard or another molecule of compound known to be in the sample or assay. If the levels are assessed as relative to a standard or internal standard, the standard may be added to the test sample prior to, during or after sample or assay processing.

To assess levels of miR-184 in the RPE cells in a subject, a sample of RPE is taken from or obtained from the subject. The sample may or may not processed prior assaying levels of the miR-184. For example, the RPE cells may be obtained from a subject and the RPE cells may then be expanded ("expanded sample") in culture to provide many more cells on which to run the assays. In this manner, only a small number of RPE cells need to be obtained from the subject to perform numerous tests and assays, including but not limited to those diagnostic and monitoring methods described herein. The sample and/or the expanded sample may or may not be stored, e.g., frozen, prior to processing or analysis.

Methods and assays designed to measure miR-184 levels are well-known in the art. In one embodiment, the miR-184 levels are assessed directly such as Northern blot analysis, or indirectly such as reverse transcribing the RNA to create a cDNA copy of the miR-184 and subsequently measuring the levels of the cDNA copies. Still other ways of measuring miR-184 levels include microarrays and dot blots. The novelty and inventiveness of the present invention are not dependent on the way in which the miR-184 levels are assessed or measured. In one embodiment, the methods of determining the levels of miR-184 involve amplifying the miR-184 prior to measuring the miR-184 levels. In one specific embodiment, the methods of determining the levels of miR-184 involve amplifying the miR-184, via polymerase chain reaction (PCR), prior to measuring the miR-184 levels.

In other embodiments, the measuring of miR-184 levels includes generating a cDNA from the miR-184 RNA (reverse transcribe the miR-184), where the polynucleotide sequence of the generated cDNA corresponds to the polynucleotide sequence of the miR-184. As used herein, the terms "correspond(s) to" and "corresponding to," as they relate to sequence alignment, are intended to mean enumerated positions within the query polynucleotide sequence, e.g., miR-184, and those positions that align with the reference nucleic acid. Thus, when the polynucleotide sequence of a subject miR-184 is aligned with the polynucleotide sequence of a reference miR-184, e.g., SEQ ID NO:1, the nucleotides in the subject sequence that "correspond to" certain enumerated positions of the reference sequence are those that align with these positions of the reference sequence, e.g., SEQ ID NO:1, but are not necessarily in these exact numerical positions of the reference sequence. Methods for aligning sequences for determining corresponding nucleotides between sequences are described herein. The nucleic acids that are aligned with one another need not be the same type of nucleic acid, i.e., one can be an RNA and the other can be a DNA molecule. For the sake of clarity, for purposes of "corresponding" or sequence identity in the methods used herein, the uracil ("u") base and the thymine ("t") bases are equivalent to one another such that a uracil base in RNA would be considered as the same (or identical base) as a thymine base in DNA.

The subject's miR-184 levels are compared to the miR-184 levels that are deemed to be normal miR-184 levels. To establish miR-184 levels of a normal individual, an individual or group of individuals may be first assessed or diagnosed as having normal RPE, retina or retinal function. Once established, the miR-184 levels of the individual or group of individuals can then be determined to establish "normal miR-184 levels." In one embodiment, miR-184 levels can be ascertained from the same subject when the subject is deemed to possess normal RPE, retina or retinal function with no signs (clinical or otherwise) of any such abnormality or dysfunction. In one embodiment, "normal miR-184 levels" are assessed in the same subject from whom the sample is taken prior to the onset of nneasureable, perceivable or diagnosed abnormal RPE, abnormal retina or retinal function. That is, the term "normal" with respect to miR-184 levels can be used to mean the subject's baseline miR-184 levels prior to the onset of any abnormalities. The miR-184 levels can then be reassessed periodically and compared to the subject's baseline miR-184 levels. Thus, the present invention also includes methods of monitoring the progression of RPE abnormality in a subject, with the methods comprising determining the subject's miR-184 levels more than once over a period of time, with the methods comprising measuring levels of microRNA-184 (miR-184) in RPE obtained from the subject at more than one time point and to determine if the levels of miR-184 in RPE in the subject increasing or decreasing over time. An increase in the levels of the miR-184 in the RPE over time is indicative that RPE in the subject may be improving in function or, at a minimum, the health of the RPE in the subject is not deteriorating. A decrease in the levels of miR-184 compared to normal levels of miR-184 is indicative that the health of the RPE in the subject may be worsening or not improving. In some embodiment the monitoring and diagnostic methods of the present invention will comprise determining the subject's miR-184 levels two, three, four, five, six, seven, eight, nine, 10 or even more times over a period of time, such as a year, two years, three, years, four years, five years, six years, seven years, eight years, nine years or even 10 years or longer.

The methods of monitoring a subject's risk of having or developing abnormal RPE, as well as the methods of monitoring the progression of RPE abnormality may or may not also include embodiments in which the subject's miR-184 levels are assessed during and after treatment of abnormal RPE, abnormal retina or abnormal retinal function, such as but not limited to treatment of AMD (wet or dry) or treatment of RP. In other words, the present invention also includes methods of monitoring the efficacy of treatment of abnormal RPE, abnormal retina or abnormal retinal function by assessing the subject's miR-184 levels over the course of the treatment and after the treatment. The treatment may be any treatment designed to improve abnormal RPE, abnormal retina or abnormal retinal function in a subject in need of treatment of abnormal RPE, abnormal retina or abnormal retinal function. Specifically, the present invention also relates to methods of monitoring the effectiveness of an ocular therapy, such as a treatment for AMD (wet or dry) or RP in a subject receiving the ocular therapy, with the methods comprising measuring levels of miR-184 in RPE obtained from the subject receiving the ocular therapy at various time points, and comparing the measured levels of the miR-184 in the RPE at two or more different time points to determine if the levels of miR-184 in RPE in the subject receiving the ocular therapy are increasing over time. An increase in the levels of the miR-184 in the RPE over time may be indicative that the ocular therapy is not ineffective. A decrease in the levels of miR-184 over time may be indicative that the ocular therapy is not effective.

In another embodiment, normal miR-184 levels are assessed in a sample of RPE cells from a different subject or patient (from the subject being analyzed) and this different subject does not have or is not suspected of having abnormal RPE, abnormal retina or abnormal retinal function. In still another embodiment, normal miR-184 levels are assessed in a population of healthy individuals, the constituents of which display no signs of abnormal RPE, abnormal retina or abnormal retinal function. Thus, the subject's miR-184 levels can be compared to normal miR-184 values generated from a single normal sample or normal miR-184 values generated from more than one normal sample.

Of course, normal levels miR-184 can fall within a range of values, and values that do not fall within this "normal range" are said to be outside the normal range. These measurements may or may not be converted to a value, number, factor or score as compared to measurements in the "normal range." For example, measured miR-184 levels that are below the normal range, may be assigned a value or −1, −2, −3, etc., depending on the scoring system devised.

The present invention also relates to methods of determining if a subject having an RPE has an increased risk of the RPE becoming abnormal, with the methods comprising measuring levels of miR-184 in RPE obtained from the subject, and comparing the measured levels of miR-184 in the RPE obtained from the subject with normal levels of miR-184, to determine if the subject's levels of miR-184 in RPE are reduced compared to the normal levels of miR-184. A decrease in the levels of miR-184 compared to normal levels of miR-184 is indicative that the RPE of the subject is at risk of becoming abnormal.

As used herein, the phrase "increased risk of the RPE becoming abnormal" is used to mean that the subject has an increased chance of developing or acquiring an abnormal RPE and/or a condition associated with an abnormal RPE compared to a normal individual. The increased risk may be relative or absolute and may be expressed qualitatively or quantitatively. For example, an increased risk may be expressed as simply determining the subject's levels of miR-184 and placing the patient in an "increased risk" category, based upon previous population studies. Alternatively, a numerical expression of the subject's increased risk may be determined based upon the miR-184 expression levels. As used herein, examples of expressions of an increased risk include but are not limited to, odds, probability, odds ratio, p-values, attributable risk, relative frequency, positive predictive value, negative predictive value, and relative risk.

If it is determined that a subject has an increased risk of developing abnormal RPE, abnormal retina or abnormal retinal function based on the methods described herein, the attending health care provider may subsequently prescribe or institute a treatment program. In this manner, the present invention also provides for methods of screening individuals as candidates for treatment of abnormal RPE, abnormal retina or abnormal retinal function, or conditions associated therewith. The attending healthcare worker may begin a prophylactic treatment regimen, based on the subject's miR-184 levels even before there are perceivable, noticeable or measurable signs of abnormal RPE, abnormal retina or abnormal retinal function in the individual.

The present invention also relates to engineered retinal pigment epithelial (RPE) cells comprising an exogenous nucleic acid coding for miR-184. The RPE cells used in the generation of engineered RPE cells need not exhibit every single characteristic of native RPE cells, but the characteristics of the RPE cells used to generate the engineered RPE cells the invention herein should be consistent with characteristics of native RPE cells. As used herein, "native RPE cells" are cells that have not been manipulated in any way and naturally exhibit the phenotypic and functional characteristics of RPE cells. Native RPE cells can be found in in vivo and in vitro environments.

As used herein, the phrase "exogenous miR-184" is used to mean that the RPE cells have more than the normal number of copies of DNA encoding the miR-184 transcript. The phrase "exogenous miR-184" can also mean that additional miR-184 transcripts have been administered to the RPE, and the miR-184 was not produced from within the cells to which the miR-184 is being administered. In general, "exogenous miR-184" can be a vector that is inserted into the genome of the RPE cells, or it can be additional copies of the miR-184 generated outside of the cell.

As used herein, "administer" or variations thereof is used to mean bringing the one or more genes or gene products into proximity to RPE cells such that the one or more genes or gene products can exert a biological effect on the RPE cells. Thus, in one embodiment of the present invention, "administer" can mean a stable or transient transfection of DNA or RNA molecule(s) into RPE cells.

As used herein, a "gene" is a DNA molecule encoding an RNA molecule that has the potential to be translated into a protein. A gene includes but is not limited to genomic DNA or cDNA and need not contain any introns. In addition, a "gene" as used in the methods of the present invention need not contain any regulatory sequences, such as, but not limited to, promoters, enhancers, UTRs and the like. Of course, the genes used in the methods and compositions of the present invention may include regulatory sequences in addition to the coding sequence. One example of a "gene" that can be used in the methods of the present invention includes, but is not limited to, an expression vector. Expression vectors and methods of making and using are well known in the art.

A "gene product" as used in the present invention includes but is not limited to an RNA molecule, e.g., an mRNA, such as miR-184, or a polypeptide or protein. The exogenous gene product, i.e., miR-184 that is administered to the RPE cells may, but need not, be produced in the RPE cells. For example, the gene product can be synthesized or generated in separate in vitro reactions and subsequently administered to the RPE cells. The mRNA gene product, if used, may but need not be a mature, fully processed mRNA. The gene products can be administered directly to the RPE cells, or the gene products can be administered indirectly through, for example, transfection of a DNA molecule into the RPE cells that, when transcribed, can produce the desired gene product.

In another embodiment, administer can mean adding or including the one or more genes or gene products in the cell culture medium of the RPE or non-RPE cells. In one embodiment, one or more gene products, for example miR-184, is transfected into the RPE cells. Such methods of mRNA transfections are well known in the art and commercially available kits can be used to transfect the RPE cells with RNA (STEMGENT, Cambridge, Mass., USA). The genes or gene products can be administered one or more times to the RPE cells. In another embodiment, the genes or gene products can be administered continuously to the RPE cells. Continuous administration would include but is not limited to maintaining or including the genes or gene products in fresh cell culture medium after passage.

In one embodiment, methods of generating the engineered RPE cells can be performed in culture. When performed in culture, standard, well-known methods for culturing RPE and can be used. In one specific embodiment, the RPE cells are initially seeded onto cell culture surfaces without any matrix or cellular scaffold being present. In another embodiment, the RPE cells are initially seeded onto cell culture surfaces with a matrix or cellular scaffold being present. Cellular scaffold and matrices for culturing RPE and RPE cells are well known in the art. For example, Thompson, H. A., et al., *J. Biomed. Mat. Res.* A, 95A(4):1233-1243 (2010) and Lu, L., et al., *Biomaterials,* 22:3345-3355 (2001), both of which are incorporated by reference, disclose matrices upon which RPE cells can be cultured. Other cell culture matrices include, but are not limited to MATRIGEL™, collagen, laminin, fibronectin and the like.

In another embodiment, the cells that are used to generate the engineered RPE cells of the present invention can initially be non-RPE cells and converted to functional RPE cells prior to engineering them with an exogenous nucleic acid encoding miR-184.

As used herein "non-RPE cells" are cells that do not have all three characteristics of the ability to perform phagocytosis, expression of melanin and expression of RPE65. It is, however, possible that the non-RPE cells used in the methods of the present invention may exhibit one or more phenotypic or functional characteristics of native RPE cells. In one embodiment, the non-RPE cells used in the methods of the present invention do not express RPE65. In another embodiment, the non-RPE cells used in the methods of the present invention do not express melanin. In another embodiment, the non-RPE cells used in the methods of the present invention do not express melanin and do not express RPE65. In yet another embodiment, the non-RPE cells used in the methods of the present invention do not have the ability to perform phagocytosis, do not express melanin and do not express RPE65.

Methods of assessing functional characteristics of cells, for example to determine if cells are functional RPE cells or non-RPE cells, are well known in the art. For example, in vitro assays utilizing latex beads can be used to assess the ability of cells to perform phagocytosis. See Kilmanskaya, I., *Meth. Enzymol.,* 418:169-194 (2006), which is incorporated by reference. Other in vitro phagocytosis assays include, but are not limited to, phagocytosis assays utilizing rod outer segments as described in Finnemann, S., et al., *Proc. Nat'l. Acad. Sci.,* 94(24):12932-12937 (1997), which is incorporated by reference. In addition, polarity assays, for example to if the Na+/K+ ATPase is located on the apical portion of the plasma membrane, are well known in the art and are discussed in Kokkinaki, M., et al., *Stem Cells,* 29:825-835 (2011), which is incorporated by reference.

In one embodiment, the non-RPE cells used in the methods of the present invention are neither embryonic stem cells, nor are they induced pluripotent stem cells (iPSCs). In another embodiment, the non-RPE cells are not adult stem cells. In another embodiment, the non-RPE cells are mesenchymal stem cells. In another embodiment, the non-RPE cells are fibroblasts or epithelial cells. The non-RPE fibroblasts used in the methods of the present invention can be derived from any connective tissue, including but not limited to, dermis, adipose, bone and cartilage. In one specific embodiment, the non-RPE fibroblasts cells are dermal fibroblasts. In another embodiment, the non-RPE cells are epithelial cells. The non-RPE epithelial cells used in the methods of the present invention can be derived from any epithelial tissue including, but not limited to, digestive system epithelium, skin epithelium, respiratory system epithelium, reproductive system epithelium and urinary system epithelium to name a few.

The methods of generating functional RPE from non-RPE cells comprise administering at least one gene or gene product to non-RPE cells in an amount sufficient to transform the non-RPE cells into functional RPE cells, wherein the at least one gene or gene product is selected from the group consisting of Pax6, OTX2, LHX2, Six3, Six6, Sox9, Nr2f2, ENTPD2, ELF3 and MITE.

In one embodiment, the methods of the present invention can be performed in culture. When performed in culture, standard, well-known methods for culturing non-RPE can be used. In one specific embodiment, the non-RPE cells are initially seeded onto cell culture surfaces without any matrix or cellular scaffold being present. In another embodiment, the non-RPE cells are initially seeded onto cell culture surfaces with a matrix or cellular scaffold being present. Cellular scaffold and matrices for culturing RPE and non-RPE cells are well known in the art. For example, Thompson, H. A., et al., *J. Biomed. Mat. Res.* A, 95A(4):1233-1243 (2010) and Lu, L., et al., *Biomaterials,* 22:3345-3355 (2001), both of which are incorporated by reference, disclose matrices upon which RPE cells can be cultured. Other cell culture matrices include, but are not limited to MATRIGEL™, collagen, laminin, fibronectin and the like.

The methods include administering any combination of one or more of these genes or gene products. For example, genes or gene products of each of Pax6, OTX2, LHX2, Six3, Six6, Sox9, Nrf2f, ENTPD2, ELF3 and MITE can be administered alone to the non-RPE cells. In another embodiment, genes or gene products of Nrf2f and ENTPD2 can be administered to the non-RPE cells. In another embodiment, genes or gene products of Nrf2f, ENTPD2 and ELF3 can be administered to the non-RPE cells. In another embodiment, genes or gene products of Nrf2f, ENTPD2, ELF3 and MITE can be administered to the non-RPE cells. In another embodiment, genes or gene products of Nrf2f and ELF3 can be administered to the non-RPE cells. In another embodiment, genes or gene products of Nrf2f, ELF3 and MITE can be administered to the non-RPE cells. In another embodiment, genes or gene products of Nrf2f and MITE can be administered to the non-RPE cells. In another embodiment, genes or gene products of Nrf2f, ENTPD2 and MITE can be administered to the non-RPE cells. In another embodiment, genes or gene products of ENTPD2 and ELF3 can be administered to the non-RPE cells. In another embodiment, genes or gene products of ENTPD2 and MITE can be administered to the non-RPE cells. In another embodiment, genes or gene products of ENTPD2, ELF3 and MITE can be administered to the non-RPE cells. In another embodiment, genes or gene products of ELF3 and MITE can be administered to the non-RPE cells.

The source of the non-RPE cells, if used, can be any animal source; for example the source of the non-RPE cells can be human, non-human primate, canine, porcine, feline, bovine, equine rodent. In general, the source of the cells, i.e., human, mouse, etc., would determine the source of the genes or gene products that are administered to the non-RPE cells. For example, a human gene encoding ENTPD2 would be administered to human non-RPE cells. This matching of the source gene or gene product with the source cells, however, is not necessary. For example, a mouse ENTPD2 gene or gene product may be administered to non-RPE cells derived from a source other than a mouse, e.g. a rat or human. If more than one gene or gene product is administered to the non-RPE cells, the administration of the genes or gene product can be sequentially or concurrently, and not all the genes or gene products need be from the same animal source.

The present invention also comprises vectors containing the nucleic acids encoding miR-184. As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagennids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. An expression vector is one into which a desired DNA sequence may be inserted by restriction and ligation such that it is operably joined to regulatory sequences and may be expressed as an RNA transcript. Vectors may further contain one or more marker sequences suitable for use in the identification and selection of cells which have been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Examples of vectors include but are not limited to those capable of autonomous replication and expression of the structural gene products present in the DNA segments to which they are operably joined.

In certain respects, the vectors to be used are those for expression of miR-184 in a host cell. Generally, such vectors comprise cis-acting control regions effective for expression in a host operatively linked to the polynucleotide to be expressed. Appropriate trans-acting factors are supplied by the host, supplied by a complementing vector or supplied by the vector itself upon introduction into the host.

A great variety of expression vectors can be used to express the proteins of the invention. Such vectors include chromosomal, episomal and virus-derived vectors, e.g., vectors derived from bacterial plasmids, from bacteriophage, from yeast episomes, from yeast chromosomal elements, from viruses such as adeno-associated virus, lentivirus, baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. All may be used for expression in accordance with this aspect of the present invention. Generally, any vector suitable to maintain, propagate or the fusion proteins in a host may be used for expression in this regard.

The DNA sequence in the expression vector is generally operably linked to appropriate expression control sequence(s) including, for instance, a promoter to direct mRNA transcription. Typically, an appropriate promoter is chosen for its suitability to drive expression in the chosen host cell, e.g., a mammalian cell. Representatives of such promoters include, but are not limited to, the phage lambda PL promoter, the E. coli lac, trp and tac promoters, HIV promoters, the SV40 early and late promoters and promoters of retroviral LTRs, to name just a few of the well-known promoters.

The promoter can function ubiquitously or tissue-specifically. Examples of non-tissue specific promoters include but are not limited to the early cytomegalovirus (CMV) promoter (described in U.S. Pat. No. 4,168,062) and Rous Sarcoma virus promoter (described in Norton and Coffin, Molec. Cell Biol. 5:281 (1985)). Tissue specific promoters for driving expression of miR-184 in RPE can also be chosen. For example, the promoters for Pax6, OTX2, LHX2, Six3, Six6, Sox9, Nrf2f, ENTPD2, ELF3 and MITE can be used to drive expression of the exogenous miR-184 in RPE. Inhibitors of some miRNAs could be used to restore miR-184 expression. miR-184 protein administration via specific bioengineered vesicles targeting RPE could be used to restore miR-184 levels in RPE. In addition, the miR-184 gene can be cloned in a vector for overexpression of miR-184 in the cells In general, expression constructs will contain sites for transcription, initiation and termination and, in the transcribed region, a ribosome binding site for translation. The coding portion of the mature transcripts expressed by the constructs will include a translation initiating AUG at the beginning and a termination codon (UAA, UGA or UAG) appropriately positioned at the end of the polypeptide to be translated. In addition, the constructs may contain control regions that regulate, as well as engender expression. Generally, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors may contain one or more selectable marker genes to provide a phenotypic trait for selection of transformed host cells. Preferred markers include dihydrofolate reductase or neomycin resistance for eukaryotic cell culture, and tetracycline, kanamycin or ampicillin resistance genes for culturing E. coli and other bacteria.

Promoter/enhancer elements which may be used to control expression of inserted sequences include, but are not limited to the SV40 early promoter region (Bernoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42) for expression in animal cells, the promoters of lactamase (Villa-Kamaroff et al., 1978, Proc. Natl. Acad. Sci. U.S.A. 75:3727-3731), tac (DeBoer et al., 1983, Proc. Natl. Acad. Sci. U.S.A. 80:21-25), or trc for expression in bacterial cells (see also "Useful proteins from recombinant bacteria" in Scientific American, 1980, 242:74-94).

Any method known in the art for inserting DNA fragments into a vector may be used to construct expression vectors containing an miR-184 encoding nucleic acid molecule comprising appropriate transcriptional/translational control signals and the polypeptide coding sequences. These methods may include in vitro recombinant DNA and synthetic techniques and in vivo recombination.

As used herein and unless otherwise indicated, the phrase "therapeutically effective amount" of a composition of the invention is measured by the therapeutic effectiveness of a compound of the invention, wherein at least one adverse effect of a disorder or condition is ameliorated or alleviated.

Nucleic acid molecules (DNA or RNA) of the invention can be administered for therapeutic or prophylactic purposes. A composition of the invention can contain one or several nucleic acid molecules of the invention. Formulations of nucleic acid molecules for therapeutic and prophylactic purposes include sterile saline or sterile buffered saline colloidal dispersion systems, such as macromolecule complexes, nanocapsules, silica microparticles, tungsten microparticles, gold microparticles, microspheres, beads and lipid based systems including oil-in-water emulsions, micelles, mixed micelles and liposomes. A colloidal system for use as a delivery vehicle in vitro and in vivo is a liposome (i.e., an artificial vesicle). The uptake of naked nucleic acid molecules may be increased by incorporating the nucleic acid molecules into and/or onto biodegradable beads, which are efficiently transported into the cells. The preparation and use of such systems is well known in the art.

A nucleic acid molecule can be associated with agents that assist in cellular uptake. It can be formulated with a chemical agent that modifies the cellular permeability, such as bupivacaine (see, e.g., WO 94/16737).

Cationic lipids are also known in the art and are commonly used for DNA delivery. Such lipids include LIPOFECTIN™, also known as DOTMA (N-[1-(2,3-dioleyloxy) propyl]-N,N,N-trimethylammonium chloride), DOTAP (1,2-bis(oleyloxy)-3-(trimethylammonio)propane, DDAB (dimethyldioctadecylammonium bromide), DOGS (dioctadecylamidologlycy spermine) and cholesterol derivatives such as DC-Chol (3 beta-(N—(N',N'-dimethyl aminomethane)-carbamoyl) cholesterol. A description of these cationic lipids can be found in EP 187,702, WO 90/11092, U.S. Pat. No. 5,283,185, WO 91/15501, WO 95/26356, and U.S. Pat. No. 5,527,928. Cationic lipids for DNA delivery can be used in association with a neutral lipid such as DOPE (dioleyl phosphatidylethanolamine) as described in, e.g., WO 90/11092.

Other transfection facilitation compounds can be added to a formulation containing cationic liposomes. They include, e.g., spermine derivatives useful for facilitating the transport of DNA through the nuclear membrane (see, for example, WO 93/18759) and membrane-permeabilizing compounds such as GAL4, Gramicidine S and cationic bile salts (see, for example, WO 93/19768).

The amount of nucleic acid molecule to be used in a formulation depends, e.g., on the strength of the promoter used in the DNA construct, and the mode of administration and type of formulation. In general, a therapeutically or prophylactically effective dose from about 1 µg to about 1 mg. In one embodiment, the dose of from about 10 µg to about 800 µg, and more specifically from about 25 µg to about 250 µg, can be administered to human adults. The administration can be achieved in a single dose or repeated at intervals.

The route of administration can be any conventional route used in the field. As general guidance, a nucleic acid molecule of the invention can be administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intra-epidermal or intramuscular route. The choice of administration will depend on the formulation that is selected.

The present invention also relates to methods of treating abnormal retinal pigment epithelium (RPE) in a subject in need of treatment thereof, the method comprising administering to the subject a therapeutically effective amount of miR-184. In one embodiment, the subject in need of treatment an abnormal RPE has been diagnosed with AMD (wet or dry) or RP prior to being treated for abnormal RPE.

The examples herein are meant to be illustrative in nature and are not intended to limit the scope of the invention.

EXAMPLES

Proteomics miR-184 expressed in RPE cells was inhibited with 10 pmoles of hsa-miR-184 mirVana™ miRNA Inhibitor (Invitrogen, Carlsbad, Calif.) per 500,000 cells. The control cells were transfected with High GC Duplex scrambled siRNA (Invitrogen, Carlsbad, Calif.). The cells were incubated for 72 hrs at 37° C. at 5% CO2. Proteins were extracted with RIPA lysis buffer (Cell Signaling, Danvers, Mass.), iTRAQ labeled for relative quantification, and analyzed by offline 2D chromatography coupled to QTOF mass spectrometric detection (AB Sciex, Foster City, Calif.).

RPE Cultures

Human primary cultures of RPE cells at passage 2 were purchased from ScienCell company (Carlsbad, Calif.) or established from eyes of organ donors following a protocol previously described (38). The Adult RPE19 (ARPE19) cell line was purchased from ATCC (Manassas, Va.). The RPE were cultured in EpiCM epithelial cell medium (ScienCell) as described previously (39).

Quantitative Real-Time Polymerase ChainReaction (aRT-PCR)

For the analysis of expression of human LAMP-1, EZR, and TYRO-3 genes by qRT-PCR, total RNA was extracted from RPE with the RNeasy kit (Qiagen, Germantown, Md.), treated with RNase-free DNase I (Qiagen), and reverse-transcribed with oligo-dT using the SuperScript III cDNA synthesis kit (Invitrogen, Carlsbad, Calif.) on a Veriti 96 well Thermal Cycler PCR Machine (Applied Biosystems, Foster City, Calif.). Quantitative PCR was performed with the QuantiTect SYBR Green PCR Kit (Qiagen). Specific primers for each gene were designed with the PrimerQuest software (Integrated DNA Technologies, Skokie Ill.) and the cDNA sequences of each gene (GenBank) to produce 100-250 bp PCR amplicons that span one or more exon/intron boundaries. Human GAPDH gene expression was analyzed in parallel, for normalization. For the analysis of expression of MIR-184, microRNA samples isolated from cultured RPE or HeLa cells using the mirVana miRNA isolation kit (Invitrogen), were reverse transcribed and amplified with the miRCURY™ Universal RT microRNA cDNA PCR kit (Exiqon, Woburn, Mass.). Quantitative PCR was performed with the miRCURY™ Universal RT microRNA PCR SYBR Green Master Mix (Exiqon, Woburn, Mass.) and MIR-184 amplification primers (Qiagen). The expression of human 5S rRNA gene was analyzed in parallel for normalization. The normalized relative expression levels for each gene were calculated with the ΔΔCt method (40).

Transfection Assays

Nucleofections of plasmid DNAs, siRNAs or the mir-184 inhibitor in HeLa or RPE cells were performed with the Amaxa Biosystems Nucleofector 11 (Lonza, Allendale, N.J.). 1 microgram of plasmid DNA, 90 pmoles of siRNA or 10 pmoles of the mir-184 inhibitor were used to transfect 5×105 cells using the high efficiency 1-013 protocol and the Basic Nucleofector Kit for Primary Mammalian Epithelial Cells Solution Mix (Cat. No VP1-1005) from Lonza.

Luciferase Assays

HeLa cells were co-transfected by nucleofection with: a) a plasmid containing the human MIR-184 gene in the pEZX-M04 vector, and b) a Luciferase-EZR-3'UTR construct in pEZX-M01 vector (both from GeneCopoeia, Rockville, Md.). The bioluminescence from the expression of firefly luciferase normalized to renilla luciferase for cell quantity variation, was quantified by MicroLumatPlus LB 96V (Berthold Technologies, Oak Ridge, Tenn.) in the absence and presence of ectopically expressed MIR-184 gene.

Antibodies

Rabbit anti-beta actin (Cell Signaling, Danvers, Mass.), mouse anti-LAMP-1 (BD Biosciences, San Jose, Calif.), rabbit anti-EZR Rabbit, and Rabbit anti-TYRO-3 (primary antibodies); Goat anti-rabbit IgG-HRP linked and goat anti-mouse IgG-HRP linked (Cell Signaling, Danvers, Mass.) (secondary antibodies).

Immunoblot Analysis

Protein samples were extracted in radioimmunoprecipitation assay (RIPA) buffer (1% NP40, 0.5% sodium deoxycolate and 1% SDS in 1× Phosphate Buffered Saline), containing freshly added Protease and Phosphatase Inhibitor Cocktail Tablets (Roche Applied Science), 1× Protease Inhibitor Cocktail Set I (EMD Millipore), 1 mM sodium vanadate, 50 mM sodium fluoride, 1 mM Phenyl Methane Sulphonyl Fluoride (PMSF) (Sigma Aldrich). Protein concentrations were measured by Bradford assay (Bio-Rad) on an Ultramak Microplate Imaging system (Bio-Rad, Hercules, Calif.). Denatured protein samples were separated using the NuPAGE electrophoresis system (Novex 4-12% Bis-Tris gels from Invitrogen) and transferred to an Amersham™ Hybrid™-ECL nitrocellulose membrane (GE Healthcare, Little Chalfont, UK) using the XCell western blot system (Invitrogen). Primary antibodies were diluted 1/1000 in 5% BSA-1×TBST and incubated for 16-20 hrs at 4° C., and secondary antibodies were diluted 1/3000 in 5% non-fat milk 1×TBST and incubated for 90 min at room temperature, based on the manufacturer's instructions. Immunoreactive protein bands were visualized by the SuperSignal® West Dura Chemiluminescent Substrate (PIERCE, Rockford, Ill.) followed by imaging with the myECL imager (Thermo Scientific Inc., Waltham, Mass.).

Phagocytosis Assays

The RPE monolayers after treatment of hsa-miR-184 mirVana™ miRNA inhibitor or control untreated RPE, were grown to confluency for 20 hrs on black flat-bottom 96-well plates (50,000 cells/well) in EpiCM medium without serum. Phagocytosis was assayed by adding 200 μg Alexa Fluor 488-conjugated Zymosan (Invitrogen, Carlsbad, Calif.) for 1 hr and quantified by fluorometry using the Vybrant Phagocytosis Assay (Invitrogen) and the Wallace 1420 Victor2 Multilabel Counter (Perkin Elmer, Waltham, Mass.). RPE cell viability was measured with the PrestoBlue Cell Viability Reagent (Invitrogen) and quantified by fluorometry for normalization.

Immunoprecipitation

ARPE19 were lysed in RIPA buffer as described above and immediately processed for immunoprecipitation with the anti-EZR antibody. The protein samples were precleared with protein-A agarose beads following the manufacturer's instructions (Cell Signaling). Protein concentration was measured by the Bradford assay (Bio-Rad, Berkley, Calif.) and was adjusted at 1 mg/ml. Homogenates containing 300 μg of total protein were incubated with the antibody to EZR diluted 1:1000 for 16 hrs at 4° C., and then protein-A agarose beads were added for 2 hrs. The immunoprecipitates (IP) were rinsed in lysis buffer three times and then subjected to immunoblot analysis with anti-EZR and anti-LAMP-1 antibodies. The 'input' protein lysates were also analyzed by immuno-blot with anti-beta actin for cell count normalization.

Results miR-184 is highly evolutionarily conserved among many species from insects to humans (FIG. 1A). In order to determine the genes and proteins that are regulated by miR-184, proteomic analysis was performed after transfecting the primary culture of human RPE with miRNA inhibitor. Proteomics revealed a large list of proteins that were either up- or down-regulated when miR-184 was inhibited. Within the proteins that showed significantly increased expression, Ezrin (EZR), showed the highest increase, by 2.12-fold.

As shown in FIG. 18 by qRT-PCR, MIR-184 is expressed in human primary RPE culture and ARPE19, but not in HeLa cells. Therefore, HeLa cells were used to study the ectopic overexpression of miR-184 by transfection. To study the interaction of EZR with miR-184, HeLa were transfected cells with Luciferase-EZR-3'UTR plasmid construct, MIR-184 plasmid construct, or with both Luciferase-EZR-3'UTR and MIR-184 plasmid constructs for 48 hrs followed by bioluminescence assay. The data revealed that the HeLa cells transfected with Luciferase-EZR-3'UTR constructs showed increase in the luciferase activity, whereas this activity was significantly inhibited (P<0.01) when HeLa cells were transfected with both Luciferase-EZR-3'UTR and MIR-184 plasmid constructs, suggesting a direct interaction between 3'UTR of EZR and miR-184, down-regulating EZR expression (FIG. 2A). To further confirm the inhibitory effect of miR-184 on EZR, ARPE19 cells were transfected with Luciferase-EZR-3'UTR construct alone, or with both Luciferase-EZR-3'UTR and miRNA-184 inhibitor followed by bioluminescence assay. The data showed that ectopic inhibition of miR-184 significantly increased EZR expression in ARPE19 compared to EZR expression in ARPE19 transfected with Luciferase-EZR-3'UTR construct alone and in the presence of endogenous miR-184 only (P<0.01) (FIG. 2B). The interaction of miR-184 and the EZR-mRNA 3'UTR is further supported by the existence of a putative binding site sequence for the miR-184 seed sequence (GGACGGA) from nucleotides 521 to 525 in the EZR-3'UTR (FIG. 2C).

Recent studies have shown an important role for EZR in regulating phagosome maturation and phago-lysosomal fusion therefore regulating phagocytosis (33,41). Other studies have reported that EZR can promote morphogenesis of apical microvilli and basal infoldings in RPE, and is required for microvilli formation in mouse RPE (42,43). To investigate the role of miR-184 in regulating an EZR-dependent RPE function such as phagocytosis, ARPE19 cells were transfected with miR-184 inhibitor for 72 hrs and analyzed in a phagocytosis assay. In parallel, to verify the MIR-184 gene silencing by the miR-184 inhibitor, the expression of MIR-184 was assayed by qRTPCR and showed that it is undetectable 72 h after transfection (FIG. 3A). The phagocytosis assay showed that inhibition of miRNA significantly reduced phagocytosis in ARPE19 compared to the cells transfected with control siRNA (P<0.01), while the cell viability was not affected (FIG. 3B). To delineate the mechanisms by which miR-184 regulates phagocytosis, ARPE19 cells were transfected with miR-184 inhibitor and analyzed the mRNA expression of genes important for phagocytosis, such as LAMP-1, MERTK, TYRO3, and AXL. The data in FIG. 3C show that miR-184 regulates EZR, LAMP-1, and TYRO3 but not MERTK and AXL mRNAs. EZR mRNA was significantly up-regulated (P<0.01), while LAMP-1 and TYRO3 mRNAs were significantly down-regulated (P<0.01 and P<0.01, respectively) in ARPE19 transfected with miR-184 inhibitor compared to cells transfected with the control siRNA (FIG. 3C). Western blot analysis of the ARPE19 cells treated similarly confirmed the up-regulation of EZR protein and the down-regulation of LAMP-1 protein in ARPE19 transfected with miR-184 inhibitor compared to the control cells; TYRO3 protein expression level did not reflect the effect observed at the transcription level (FIG. 3D).

A recent study revealed the direct molecular interaction of EZR with LAMP-1 in human melanoma cells (31). To assess the interaction of EZR and LAMP-1 and the role of miR-184 in regulating their optimal interaction in human RPE, ARPE19 cells were transfected with scrambled siRNA and miR-184, performed immunoprecipitation of EZR followed by immunoblotting with LAMP-1 antibody and confirmed the EZR and LAMP-1 interaction. However, this interaction was significantly downregulated in the ARPE19 transfected with miR-184 hairpin (inhibitor of miR-184), probably due to down-regulation of total LAMP-1 protein level and therefore its lower availability to interact with EZR (FIG. 3E). Together the data show that miR-184 regulates the expression of pivotal genes and proteins involved in phagocytosis and indirectly control the phagocytosis pathway in human RPE.

Recent studies have shown critical roles for miRNAs in a variety of diseases (44). Two independent studies have reported on the regulation of angiogenesis and choroidal neovascularization by miRNAs (45,46). miRNAs are also presented as potential therapeutic targets for AMD (47). To investigate the involvement of miR-184 in the pathophysiology of AMD, qRT-PCR was performed to detect the MIR-184 mRNA levels in human primary RPE cultures from 4 AMD and 4 age-matched normal donors. The data showed that miR-184 is significantly inhibited in the RPE from AMD donors and in two AMD samples (AMD 9 and 14), the MIR-184 expression is undetectable by qRT-PCR (FIG. 4A). In addition, the expression of LAMP-1 was significantly down-regulated in the AMD samples (FIG. 4B). It was observed that a direct correlation existed between the lowest expression levels of MIR-184 and inhibition of LAMP-1 mRNA levels in the AMD samples (FIGS. 4A-4B, AMD 9 and 14). In accordance with the data obtained in the ARPE-19 with the miR-184 inhibitor (FIGS. 3C-3D), these observations further support the upregulation of LAMP-1 expression by miR-184 and suggest that low levels of miR-184 can still maintain LAMP-1 expression in human RPE. Moreover, low expression levels of MIR-184 and LAMP-1 genes in the AMD RPE compared to normal RPE suggest an important role for miR-184 in the disease mechanisms of AMD.

To assess whether restoring the miR-184 levels in AMD RPE could rescue the LAMP-1 expression levels, the two AMD RPE cells with the lowest MIR-184 and LAMP-1 expression were selected and transfection was performed with the MIR-184 overexpressing plasmid construct followed by qRT-PCR and Western blot analysis. The data in FIG. 4C shows that transfection with MIR-184 overexpressing plasmid restored the levels of MIR-184 in the AMD RPE and therefore rescued the LAMP-1 mRNA levels in the transfected cells compared to non-transfected AMD RPE cells. Western blot analysis of the AMD RPE cells transfected with MIR-184 plasmid confirmed the rescue of LAMP-1 protein levels compared to non-transfected cells (FIG. 4D).

REFERENCES

All references cited above and listed below are incorporated by reference.
1. Weitzel, R. P., Lesniewski, M. L., Greco, N. J., and Laughlin, M. J. (2011), *Leukemia* 25, 169-172.
2. Ryan, D. G., Oliveira-Fernandes, M., and Lavker, R. M. (2006), *Mol Vis* 12, 1175-1184.
3. Nomura, T., Kimura, M., Horii, T., Morita, S., Soejima, H., Kudo, S., and Hatada, I. (2008) *Human molecular genetics* 17, 1192-1199.
4. Liu, C., Teng, Z. Q., Santistevan, N. J., Szulwach, K. E., Guo, W., Jin, P., and Zhao, X. (2010) *Cell Stem Cell* 6, 433-444.
5. Foley, N. H., Bray, I. M., Tivnan, A., Bryan, K., Murphy, D. M., Buckley, P. G., Ryan, J., O'Meara, A., O'Sullivan, M., and Stallings, R. L. (2010), *Molecular cancer* 9, 83.
6. Tivnan, A., Foley, N. H., Tracey, L., Davidoff, A. M., and Stallings, R. L. (2010) *Anticancer research* 30, 4391-4395.
7. Gehrke, S., Imai, Y., Sokol, N., and Lu, B. (2010) *Nature* 466, 637-641.
8. McKiernan, R. C., Jimenez-Mateos, E. M., Sano, T., Bray, I., Stallings, R. L., Simon, R. P., and Henshall, D. C. (2012) *Experimental neurology* 237, 346-354.
9. Shalom-Feuerstein, R., Serror, L., De La Forest Divonne, S., Petit, I., Aberdam, E., Camargo, L., Damour, O., Vigouroux, C., Solomon, A., Gaggioli, C., Itskovitz-Eldor, J., Ahmad, S., and Aberdam, D. (2012) *Stem Cells* 30, 898-909.
10. Li, P., Peng, J., Hu, J., Xu, Z., Xie, W., and Yuan, L. (2011) *Molecular biology reports* 38, 355-358.
11. Iovino, N., Pane, A., and Gaul, U. (2009) *Developmental cell* 17, 123-133.
12. Finnemann, S. C. (2003) *The EMBO journal* 22, 4143-4154.
13. Strauss, O. (2005) *Physiological Reviews* 85, 845-881.
14. Rizzolo, L. J. (1997) *Histology and histopathology* 12, 1057-1067.
15. Steinberg, R. H. (1985) *Advances in ophthalmology* 60, 327-346.
16. Bok, D. (1993) *Journal of cell science. Supplement* 17, 189-195.
17. Boulton, M., and Dayhaw-Barker, P. (2001) *Eye (Lond)* 15, 384-389.
18. Mata, N. L., and Tsin, A. T. (1998) *Biochimica et biophysica acta* 1394, 16-22.
19. Baehr, W., Wu, S. M., Bird, A. C., and Palczewski, K. (2003) *Vision research* 43, 2957-2958.
20. Besch, D., Jagle, H., Scholl, H. P., Seeliger, M. W., and Zrenner, E. (2003) *Vision research* 43, 3095-3108.
21. Dornonville de la Cour, M. (1993) *Acta ophthalmologica Supplement*, 1-32.
22. Ishida, K., Panjwani, N., Cao, Z., and Streilein, J. W. (2003) *Ocular immunology and inflammation* 11, 91-105.

23. Adamis, A. P., Shima, D. T., Yeo, K. T., Yeo, T. K., Brown, L. F., Berse, B., D'Amore, P. A., and Folkman, J. (1993) *Biochem Biophys Res Commun* 193, 631-638.
24. Becerra, S. P., Fariss, R. N., Wu, Y. Q., Montuenga, L. M., Wong, P., and Pfeffer, B. A. (2004) *Exp Eye Res* 78, 223-234.
25. Tsukita, S., and Yonemura, S. (1997) *Current opinion in cell biology* 9, 70-75.
26. Gimeno, L., Corradi, A., Cobos, I., Consalez, G. G., and Martinez, S. (2004) *Gene expression patterns: GEP* 4, 749-754.
27. Gould, K. L., Bretscher, A., Esch, F. S., and Hunter, T. (1989) *The EMBO journal* 8, 4133-4142.
28. Ma, L., and Jiang, T. (2013) *Oncology reports* 30, 1899-1905.
29. Ren, L., Hong, S. H., Chen, Q. R., Briggs, J., Cassavaugh, J., Srinivasan, S., Lizardo, M. M., Mendoza, A., Xia, A. Y., Avadhani, N., Khan, J., and Khanna, C. (2012) *Cancer research* 72, 1001-1012.
30. Osawa, H., Smith, C. A., Ra, Y. S., Kongkham, P., and Rutka, J. T. (2009) *Neuro-oncology* 11, 381-393.
31. Federici, C., Brambilla, D., Lozupone, F., Matarrese, P., de Milito, A., Lugini, L., Iessi, E., Cecchetti, S., Marino, M., Perdicchio, M., Logozzi, M., Spada, M., Malorni, W., and Fais, S. (2009) *International journal of cancer. Journal international du cancer* 124, 2804-2812.
32. Legg, J. W., and Isacke, C. M. (1998) *Current biology: CB* 8, 705-708.
33. Marion, S., Hoffmann, E., Holzer, D., Le Clainche, C., Martin, M., Sachse, M., Ganeva, I., Mangeat, P., and Griffiths, G. (2011) *Traffic* 12, 421-437.
34. Huynh, K. K., Eskelinen, E. L., Scott, C. C., Malevanets, A., Saftig, P., and Grinstein, S. (2007) *The EMBO journal* 26, 313-324.
35. Eskelinen, E. L. (2006) *Molecular aspects of medicine* 27, 495-502.
36. Cook, N. R., Row, P. E., and Davidson, H. W. (2004) *Traffic* 5, 685-699.
37. Wang, F. E., Zhang, C., Maminishkis, A., Dong, L., Zhi, C., Li, R., Zhao, J., Majerciak, V., Gaur, A. B., Chen, S., and Miller, S. S. (2010) *FASEB journal: official publication of the Federation of American Societies for Experimental Biology* 24, 1552-1571.
38. Maminishkis, A., Chen, S., Jalickee, S., Banzon, T., Shi, G., Wang, F. E., Ehalt, T., Hammer, J. A., and Miller, S. S. (2006) *Invest Ophthalmol Vis Sci* 47, 3612-3624.
39. Kokkinaki, M., Sahibzada, N., and Golestaneh, N. (2011) Human iPS-Derived Retinal Pigment Epithelium (RPE) Cells Exhibit Ion Transport, Membrane Potential, Polarized VEGF Secretion and Gene Expression Pattern Similar to Native RPE. *Stem Cells*.
40. Livak, K. J., and Schmittgen, T. D. (2001) *Methods* 25, 402-408.
41. Erwig, L. P., McPhilips, K. A., Wynes, M. W., Ivetic, A., Ridley, A. J., and Henson, P. M. (2006) *Proceedings of the National Academy of Sciences of the United States of America* 103, 12825-12830.
42. Bonilha, V. L., Finnemann, S. C., and Rodriguez-Boulan, E. (1999) *The Journal of cell biology* 147, 1533-1548.
43. Bonilha, V. L., Rayborn, M. E., Saotome, I., McClatchey, A. I., and Hollyfield, J. G. (2006) *Exp Eye Res* 82, 720-729.
44. Soifer, H. S., Rossi, J. J., and Saetrom, P. (2007) *Mol Ther* 15, 2070-2079.
45. Zhou, Q., Gallagher, R., Ufret-Vincenty, R., Li, X., Olson, E. N., and Wang, S. (2011) *Proceedings of the National Academy of Sciences of the United States of America* 108, 8287-8292.
46. Shen, J., Yang, X., Xie, B., Chen, Y., Swaim, M., Hackett, S. F., and Campochiaro, P. A. (2008) *Mol Ther* 16, 1208-1216.
47. Wang, S., Koster, K. M., He, Y., and Zhou, Q. (2012) *Future medicinal chemistry* 4, 277-287.
48. Kevany, B. M., and Palczewski, K. (2010) *Physiology (Bethesda)* 25, 8-15.
49. Sun, K., Cai, H., Tezel, T. H., Paik, D., Gaillard, E. R., and Del Priore, L. V. (2007) *Mol Vis* 13, 2310-2319.
50. Li, W. (2013) Phagocyte dysfunction, tissue aging and degeneration. *Ageing research reviews*.
51. Iliff, B. W., Riazuddin, S. A., and Gottsch, J. D. (2012) *Invest Ophthalmol Vis Sci* 53, 348-353.
52. Hughes, A. E., Bradley, D. T., Campbell, M., Lechner, J., Dash, D. P., Simpson, D. A., and Willoughby, C. E. (2011) *American journal of human genetics* 89, 628-633.
53. Karali, M., Peluso, I., Gennarino, V. A., Bilio, M., Verde, R., Lago, G., Dolle, P., and Banfi, S. (2010) *BMC genomics* 11, 715.
54. Yu, J., Ryan, D. G., Getsios, S., Oliveira-Fernandes, M., Fatima, A., and Lavker, R. M. (2008) *Proceedings of the National Academy of Sciences of the United States of America* 105, 19300-19305.
55. Olivieri, F., Rippo, M. R., Monsurro, V., Salvioli, S., Capri, M., Procopio, A. D., and Franceschi, C. (2013) MicroRNAs linking inflamm-aging, cellular senescence and cancer. *Ageing research reviews*.
56. Gehrs, K., Anderson, D., Johnson, L and Hageman, G, (2006) Age-related macular degeneration—emerging pathogenetic and therapeutic concepts, *Ann. Med.* 38(7), 450-71.
57. Klein, R. Klein, B. E. Lee, K. E. Cruickshanks, K. J. and Gangnon, R. E. (2006) Changes in visual acuity in a population over a 15-year period: the Beaver Dam Eye Study. *Am J Ophthalmol.* 142(4):539-49.
58. Klein, R. Chou, C. F. Klein, B. E. Zhang, X. Meuer, S. M. and Saaddine, J. B (2011) Prevalence of age-related macular degeneration in the US population. *Arch Ophthalmol.* 129(1):75-80.
59. Rein, D. B. Wittenborn, J. S. Zhang, X. Honeycutt, A. A. Lesesne, S. B. and Saaddine, J. (2009) Forecasting age-related macular degeneration through the year 2050: the potential impact of new treatments. *Arch Ophthalmol.* 124(4):533-40.
60. Bok, D (1993) The retinal pigment epithelium: a versatile partner in vision. *J Cell Sci Suppl.* 17:189-95.
61. Boulton, M. and Dayhaw-Barker, P. (2001) The role of the retinal pigment epithelium: topographical variation and ageing changes. *Eye (Lond).* 15(Pt 3):384-9.
62. Nowak, J. Z. (2006) Age-related macular degeneration (AMD): pathogenesis and therapy. *Pharmacol Rep.* 58(3); 353-63.
63. Abdelsalam, A. Del Priore, L. and Zarbin, M. A. (1999) Drusen in age-related macular degeneration: pathogenesis, natural course, and laser photocoagulation-induced regression. *Surv Ophthalmol.* 44(1):1-29.
64. Ferris, F. L., 3rd Fine, S. L. and Hyman, L. (1984) Age-related macular degeneration and blindness due to neovascular maculopathy. *Arch Ophthalmol.* 102(11): 1640-2.

What is claimed is:

1. A method of treating a subject that has been diagnosed with age-related macular degeneration (AMD), the method comprising:
    measuring levels of microRNA-184 (miR-184) in the subject's retinal pigment epithelium (RPE) obtained from the subject, and
    administering a treatment to the subject that increases the activity or expression of miR-184 in the subject's RPE if the levels of miR-184 in the subject's RPE are lower than normal levels of miR-184, wherein the treatment comprises miR-184, or one or more expression vectors of miR-184;
    wherein the normal levels of miR-184 comprise (i) miR-184 levels in RPE from an individual or individuals who does not suffer from AMD, or (ii) miR-184 levels in RPE from the subject prior to the onset of AMD.

2. The method of claim 1, wherein the RPE obtained from the subject is expanded in culture prior to measuring levels of the miR-184.

3. The method of claim 1, wherein the measuring of the miR-184 comprises amplifying the miR-184 with a polymerase chain reaction (PCR).

4. The method of claim 3, wherein the measuring of the miR-184 comprises generating cDNA from the miR-184 and measuring levels of the cDNA, wherein the polynucleotide sequence of the cDNA corresponds to the polynucleotide sequence of the miR-184.

5. The method of claim 1, wherein the treatment comprises administering to the subject miR-184.

6. A method of treating age-related macular degeneration (AMD) in a subject in need thereof, the method comprising:
    measuring the levels of microRNA-184 (miR-184) in the retinal pigment epithelium (RPE) in the subject and
    administering an AMD treatment to the subject if the levels of miR-184 in the RPE of the subject are lower than normal levels of miR-184, wherein the AMD treatment comprises miR-184, or one or more expression vectors of miR-184;
    wherein the normal levels of miR-184 comprise (i) miR-184 levels in RPE from an individual or individuals who does not suffer from AMD, or (ii) miR-184 levels in RPE from the subject prior to the onset of AMD.

7. The method of claim 6, wherein the RPE obtained from the subject is expanded in culture prior to measuring levels of the miR-184.

8. The method of claim 6, wherein the measuring of the miR-184 comprises amplifying the miR-184 with a polymerase chain reaction (PCR).

9. The method of claim 8, wherein the measuring of the miR-184 comprises generating cDNA from the miR-184 and measuring levels of the cDNA, wherein the polynucleotide sequence of the cDNA corresponds to the polynucleotide sequence of the miR-184.

* * * * *

SEQUENCE LISTING

<160> NUMBER OF SEQ ID NOS: 13

<210> SEQ ID NO 1
<211> LENGTH: 84
<212> TYPE: RNA
<213> ORGANISM: Homo sapiens

<400> SEQUENCE: 1
ccagucacgu ccccuuauca cuuuuccagc ccagcuuugu gacuguaagu guuggacgga    60
gaacugauaa ggguagguga uuga    84

<210> SEQ ID NO 2
<211> LENGTH: 22
<212> TYPE: RNA
<213> ORGANISM: Homo sapiens

<400> SEQUENCE: 2
uggacggaga acugauaagg gu    22

<210> SEQ ID NO 3
<211> LENGTH: 22
<212> TYPE: RNA
<213> ORGANISM: Canis familiaris

<400> SEQUENCE: 3
uggacggaga acugauaagg gc    22

<210> SEQ ID NO 4
<211> LENGTH: 22
<212> TYPE: RNA
<213> ORGANISM: Culex quinquefasciatus

<400> SEQUENCE: 4
uggacggaga acugauaagg gu    22

<210> SEQ ID NO 5
<211> LENGTH: 22
<212> TYPE: RNA
<213> ORGANISM: Cricetulus griseus

<400> SEQUENCE: 5
uggacggaga acugauaagg gc    22

<210> SEQ ID NO 6
<211> LENGTH: 22
<212> TYPE: RNA
<213> ORGANISM: Cyprinus carpio

<400> SEQUENCE: 6
uggacggaga acugauaagg gu    22

<210> SEQ ID NO 7
<211> LENGTH: 22
<212> TYPE: RNA
<213> ORGANISM: Bos taurus

<400> SEQUENCE: 7
uggacggaga acugauaagg gc    22

<210> SEQ ID NO 8
<211> LENGTH: 22
<212> TYPE: RNA
<213> ORGANISM: Drosophila melanogaster

<400> SEQUENCE: 8
uggacggaga acugauaagg gu                                              22

<210> SEQ ID NO 9
<211> LENGTH: 22
<212> TYPE: RNA
<213> ORGANISM: Equus caballus

<400> SEQUENCE: 9
uggacggaga acugauaagg gu                                              22

<210> SEQ ID NO 10
<211> LENGTH: 22
<212> TYPE: RNA
<213> ORGANISM: Gallus gallus

<400> SEQUENCE: 10
uggacggaga acugauaagg gu                                              22

<210> SEQ ID NO 11
<211> LENGTH: 22
<212> TYPE: RNA
<213> ORGANISM: Mus musculus

<400> SEQUENCE: 11
uggacggaga acugauaagg gu                                              22

<210> SEQ ID NO 12
<211> LENGTH: 22
<212> TYPE: RNA
<213> ORGANISM: Pongo pygmaeus

<400> SEQUENCE: 12
uggacggaga acugauaagg gu                                              22

<210> SEQ ID NO 13
<211> LENGTH: 1196
<212> TYPE: DNA
<213> ORGANISM: Homo sapiens

<400> SEQUENCE: 13
cagccaggcc aggaccaagg gcagaggggt gctcatagcg ggcgctgcca gccccgccac      60
gcttgtgtct ttagtgctcc aagtctagga actccctcag atcccagttc ctttagaaag     120
cagttaccca acagaaacat tctgggctgg gaaccaggga ggcgccctgg tttgttttcc     180
ccagttgtaa tagtgccaag caggcctgat tctcgcgatt attctcgaat cacctcctgt     240
gttgtgctgg gagcaggact gattgaatta cggaaaatgc ctgtaaagtc tgagtaagaa     300
acttcatgct ggcctgtgtg atacaagagt cagcatcatt aaaggaaacg tggcaggact     360
tccatctgtg ccatacttgt tctgtattcg aaatgagctc aaattgattt tttaatttct     420
atgaaggatc catctttgta tatttacatg cttagagggg tgaaaattat tttggaaatt     480
gagtctgaag cactctcgca cacacagtga ttccctcctc ccgtcactcc acgcagctgg     540
cagagagcac agtgatcacc agcgtgagtg gtggaggagg acacttggat ttttttttt     600 gtttttttt tttttgctta acagttttag aatacattgt acttatacac cttattaatg     660
atcagctata tactatttat atacaagtga taatacagat ttgtaacatt agttttaaaa     720
agggaaagtt ttgttctgta tattttgtta ccttttacag aataaaagaa ttacatatga     780

```
aaaaccctct aaaccatggc acttgatgtg atgtggcagg agggcagtgg tggagctgga      840
cctgcctgct gcagtcacgt gtaaacagga ttattattag tgttttatgc atgtaatgga      900
ctatgcacac ttttaatttt gtcagattca cacatgccac tatgagcttt cagactccag      960
ctgtgaagag actctgtttg cttgtgtttg tttgtttgca gtctctctct gccatggcct     1020
tggcaggctg ctggaaggca gcttgtggag gccgttggtt ccgcccactc attccttctc     1080
gtgcactgct ttctccttca cagctaagat gccatgtgca ggtggattcc atgccgcaga     1140
catgaaataa aagctttgca aaggcacgaa gcaaaaaaaa aaaaaaaaaa aaaaaa         1196
```